United States Patent [19]

Francis et al.

[11] Patent Number: 5,444,045
[45] Date of Patent: Aug. 22, 1995

[54] METHOD OF ADMINISTERING IGF-1, IGF-2, AND ANALOGS THEREOF TO BIRDS

[75] Inventors: Geoffrey L. Francis, Athelstone SA; Paul E. Walton, Clarence Park SA; F. John Ballard, Kensington, all of Australia; John P. McMurty, Beltsville, Md.; Patricia V. Phelps, Durham, N.C.

[73] Assignees: GroPep, Pty. Ltd., Adelaide, Australia; U.S.D.A., Beltsville, Md.; Embrex, Inc., N.C.

[21] Appl. No.: 947,035

[22] Filed: Sep. 17, 1992

[51] Int. Cl.$^6$ .................. A61K 38/00; A61K 38/22; A61K 35/12; C07K 14/00

[52] U.S. Cl. .................................. 514/12; 514/21; 530/324; 530/399; 530/350

[58] Field of Search .................. 514/12, 21; 530/399, 530/324, 350

[56] References Cited

U.S. PATENT DOCUMENTS

| | | | |
|---|---|---|---|
| 4,040,388 | 8/1977 | Miller | 119/1 |
| 4,593,646 | 7/1986 | Miller et al. | 119/1 |
| 4,681,063 | 7/1987 | Hebrank | 119/1 |
| 4,876,242 | 10/1989 | Applebaum et al. | 514/3 |
| 5,028,421 | 7/1991 | Fredericksen et al. | 424/85.2 |
| 5,077,276 | 12/1991 | Ballard et al. | 514/12 |
| 5,106,617 | 4/1992 | Federicksen et al. | 424/85.2 |

FOREIGN PATENT DOCUMENTS

| | | |
|---|---|---|
| PCT/AU90/-00210 | 12/1990 | Australia . |
| 0251750 | 7/1988 | European Pat. Off. . |
| WO87/01038 | 2/1987 | WIPO . |
| WO89/05822 | 6/1989 | WIPO . |
| WO91/18621 | 12/1991 | WIPO . |

OTHER PUBLICATIONS

McGuinness, et al. "Response of Young Broiler Chickens to Chronic Injection of Recombinant-Derived Human Insulin-Like Growth Factor-I$^{1,2}$", Domestic Animal Endocrinology, 8(4):611–620, (1991).

Lima, et al., "Glucose and Insulin Regulate Insulin Sensitivity in Primary Cultured Adipocytes without Affecting Insulin Receptor Kinase Activity", Endocrinology, 128, No. 5:2415–2426 (1991).

Francis, et al., "Plasma clearance of chicken and human insulin–like growth factor–I and their association with circultaing binding proteins in chickens", Journal of Endocrinology, 124:361–370 (1990).

Tepperman, et al., Metabolic and Endocrine Physiology, Fifth Edition, 238–239 (1987).

Buonomo, et al. "Effects of Insulin–like Growth Factor I (IGF–I) on Growth Hormone–Releasing Factor (GRF) and Thyrotropin–Releasing Hormone (TRH) Stimulation of Growth Hormone (GH) Secretion in the Domestic Fowl (Gallus domesticus)", General and Comparative Endocrinology, 66: 274–279 (1987).

Huybrechts, et al., "Effect of Recombinant Human Insulin–Like Growth Factor–I on Weight Gain, Fat Content, and Hormonal Parameters in Broiler Chickens", Poultry Science, 71:181–187 (1992).

(List continued on next page.)

Primary Examiner—Jill Warden
Assistant Examiner—Lynn Touzeau
Attorney, Agent, or Firm—Bell, Seltzer, Park & Gibson

[57] ABSTRACT

A method of enhancing the growth of a bird is described. The method comprises (a) administering a compound selected from the group consisting of IGF-1, IGF-2 and active analogs thereof to a bird in ovo; then (b) incubating the bird to hatch; and then (c) growing the bird for at least three weeks after hatch. The compound is administered in ovo in an amount sufficient to enhance the growth of the bird at least three weeks after hatch. Preferred birds for practicing the present invention are chickens, and preferred compounds for practicing the present invention are IGF-1 and analogs thereof. The use of IGF-1, IGF-2 and active analogs thereof for the preparation of a medicament for administration to birds in ovo to ehance the growth of the bird at least three weeks after hatch is also disclosed, along with the pharmaceutical formulations so prepared.

35 Claims, No Drawings

OTHER PUBLICATIONS

Heaton, et al., "*Regulation of Insulin and Insulin–Like Growth Factor (IGF) Responsiveness by IGF's in Rat Hepatoma Cells*", Endocrinology, 118, No. 6:2555–2560 (1986).

Krett, et al., "*Mediation of Insulin–Like Growth Factor Actions by the Insulin Receptor in H–35 Rat Hepatoma Cells*", Endocrinology, 120, No. 1:401–408 (1987).

de Pablo, et al., "*Untoward effects of pharmacological doses of insulin in early chick embryos: through which receptor are they mediated?*", Diabetologia, 28:308–313 (1985).

de Pablo, et al., "*Insulin Antibodies Retard and Insulin Accelerates Growth and Differentiation in Early Embryos*", Diabetes, 34:1063–1067 (1985).

Gavin, III, et al., "*Insulin–Dependent Regulation of Insulin Receptor Concentrations: A Direct Demonstration in Cell Culture*", Proc. Nat. Acad. Sci. USA, 71, No. 1:84–88 (1974).

R. Vasilatos–Younken, Poultry Science 70, 1764–1780 (1991).

M. Girbau et al., Endocrinology 121, No. 4, 1477–1482 (1987).

C. Scanes et al., Growth, Development & Aging 53, 151–157 (1989).

G. S. G. Spencer et al., Reprod. Nutr. Dev. 30, 515–521 (1990).

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 70 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:1:

Gly Pro Glu Thr Leu Cys Gly Ala Glu Leu Val Asp Ala Leu Gln Phe
1               5                       10                      15

Val Cys Gly Asp Arg Gly Phe Tyr Phe Asn Lys Pro Thr Gly Tyr Gly
                20              25                      30

Ser Ser Ser Arg Arg Ala Pro Gln Thr Gly Ile Val Asp Glu Cys Cys
            35              40                  45

Phe Arg Ser Cys Asp Leu Arg Arg Leu Glu Met Tyr Cys Ala Pro Leu
    50                  55                  60

Lys Pro Ala Lys Ser Ala
65              70

( 2 ) INFORMATION FOR SEQ ID NO:2:

( i ) SEQUENCE CHARACTERISTICS:
        ( A ) LENGTH: 67 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:2:

Ala Tyr Arg Pro Ser Glu Thr Leu Cys Gly Gly Glu Leu Val Asp Thr
1               5                       10                      15

Leu Gln Phe Val Cys Gly Asp Arg Gly Phe Tyr Phe Ser Arg Pro Ala
                20              25                      30

Ser Arg Val Ser Arg Arg Ser Arg Gly Ile Val Glu Glu Cys Cys Phe
            35              40                  45

Arg Ser Cys Asp Leu Ala Leu Leu Glu Thr Tyr Cys Ala Thr Pro Ala
    50                  55                  60

Leu Ser Glu
65

( 2 ) INFORMATION FOR SEQ ID NO:3:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:3:

Val Leu Cys
1

( 2 ) INFORMATION FOR SEQ ID NO:4:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:4:

Arg Leu Cys
1

( 2 ) INFORMATION FOR SEQ ID NO:5:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:5:

Gly Leu Cys
    1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:6:

Gly Thr Leu Cys
    1

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:7:

Gly Pro Arg Thr Leu Cys
    1                    5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:8:

Gly Pro Gly Arg Leu Cys
    1                    5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (x i) SEQUENCE DESCRIPTION: SEQ ID NO:9:

Gly Pro Gly Gly Leu Cys
1               5

(2) INFORMATION FOR SEQ ID NO:10:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (i i i) HYPOTHETICAL: NO (x i) SEQUENCE DESCRIPTION: SEQ ID NO:10:

Gly Pro Gly Thr Leu Cys
1               5

(2) INFORMATION FOR SEQ ID NO:11:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (i i i) HYPOTHETICAL: NO (x i) SEQUENCE DESCRIPTION: SEQ ID NO:11:

Gly Pro Gln Thr Leu Cys
1               5

(2) INFORMATION FOR SEQ ID NO:12:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (i i i) HYPOTHETICAL: NO (x i) SEQUENCE DESCRIPTION: SEQ ID NO:12:

Gly Pro Lys Thr Leu Cys
1               5

(2) INFORMATION FOR SEQ ID NO:13:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (i i i) HYPOTHETICAL: NO (x i) SEQUENCE DESCRIPTION: SEQ ID NO:13:

Gly Pro Leu Thr Leu Cys
1               5

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:14:

Ala Tyr Arg Pro Ser Lys Thr Leu Cys
    1                      5

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:15:

Ala Tyr Arg Pro Ser Arg Thr Leu Cys
    1                      5

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:16:

Ala Tyr Arg Pro Ser Gly Arg Leu Cys
    1                      5

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:17:

Ala Tyr Arg Pro Ser Gly Thr Leu Cys
    1                      5

( 2 ) INFORMATION FOR SEQ ID NO:18:

( i ) SEQUENCE CHARACTERISTICS:
        ( A ) LENGTH: 83 amino acids
        ( B ) TYPE: amino acid
        ( C ) STRANDEDNESS: single
        ( D ) TOPOLOGY: linear ( i i ) MOLECULE TYPE: protein (iii) HYPOTHETICAL: NO (xi) SEQUENCE DESCRIPTION: SEQ ID NO:18:

```
Met Phe Pro Ala Met Pro Leu Ser Ser Leu Phe Val Asn Gly Pro Arg
 1           5                    10                      15
Thr Leu Cys Gly Ala Glu Leu Val Asp Ala Leu Gln Phe Val Cys Gly
            20                  25                  30
Asp Arg Gly Phe Tyr Phe Asn Lys Pro Thr Gly Tyr Gly Ser Ser Ser
        35                  40                  45
Arg Arg Ala Pro Gln Thr Gly Ile Val Asp Glu Cys Cys Phe Arg Ser
    50                  55              60
Cys Asp Leu Arg Arg Leu Glu Met Tyr Cys Ala Pro Leu Lys Pro Ala
 65              70                      75                  80
Lys Ser Ala
```

METHOD OF ADMINISTERING IGF-1, IGF-2, AND ANALOGS THEREOF TO BIRDS

FIELD OF THE INVENTION

The present invention relates to a method of treating birds by the in ovo administration of human insulin-like growth factor-1 (IGF-1) and human insulin-like growth factor-1 analogs.

BACKGROUND OF THE INVENTION

Physiologically active peptides such as growth factors are administered to birds in ovo to achieve a physiological effect in the birds. For example, U.S. Pat. No. 5,028,421 to Fredericksen discloses a method for increasing the weight of treated birds after hatch by introducing a T-cell growth factor into eggs on about the eighteenth day of incubation.

Current literature suggests both insulin and insulin-like growth factors are physiological regulators of embryonic growth and differentiation. Both insulin and IGF-1 affect metabolism and growth, and a variety of cells differentiate in vitro when exposed to these growth factors. See, e.g., Girbau et al., *Endocrinology* 121, 1478 (1987).

Chicken IGF-1 has been chemically purified and characterized. Some evidence correlates growth rate and endogenous circulating IGF concentrations in poultry. See, e,g., Scanes et al., *Growth Dev. Aging* 53, 151-157 (1989).

Due to the lack of availability of native or synthesized chicken IGF-1, experimental studies of the biological effects of IGF-1 in poultry have used human IGF-1. Human IGF-1 in vitro has been shown to specifically influence the metabolism, differentiation, and proliferation of cells from embryonic and posthatch chicks in vitro. See, e,g., Vasilatos-Younken and Scanes, *Poultry Science* 70, 1775 (1991).

In ovo administration of human IGF-1 to poultry has been studied previously. The effect of human IGF-1 administered into the allantois of day 7 and day 14 chick embryos was reported by Spencer et al., *Reprod. Nutr. Dev.* 30, 515-521 (1990). The posthatch data of Spencer et al. indicated that there were no significant differences between treated and control groups in weight gain or several other measures of growth. The reference concludes that the administration of exogenous IGF-1 from day 7 to day 14 does not stimulate growth in the chick embryo.

Girbau et al., *Endocrinology* 121, 1477-1482 (1987), disclose the administration of recombinant human IGF-1 to 2 day old chick embryos by injection (injection site not disclosed). The embryos were sacrificed at day 4, and various biochemical indices were compared to non-injected controls. Extracts of day 4 embryos showed accelerated development, although even greater acceleration in development was seen in embryos injected with insulin. Girbau et al. report that they believe "[t]he stereotype which considers insulin a metabolic hormone and IGF-1 a growth hormone is far too restrictive," and "that insulin and IGF-1 may have a regulatory, complementary, or overlapping role in normal chick embryo early development" which suggests a belief that administration of IGF-1 alone is not a method of enhancing growth.

SUMMARY OF THE INVENTION

A first aspect of the present invention is a method of enhancing the growth of a bird. the method comprises (a) administering a compound selected from the group consisting of insulin-like growth factor 1 (IGF-1), insulin-like growth factor 2 (IGF-2) and active analogs (i.e., agonsists) thereof to a bird in ovo; then (b) incubating said bird to hatch; and then (c) growing said bird for at least three weeks after hatch. The compound is administered in ovo in an amount sufficient to enhance the growth of said bird (e.g., as reflected by an enhancement in weight gain) at least three weeks (preferably even four weeks and five weeks) after hatch. The compound may be administered at any time during in ovo incubation. For example, the compound is, in one embodiment, administered to said egg during the first quarter of incubation, and in another embodiment is administered to said egg during the last quarter of incubation.

A second aspect of the present invention is the use of IGF-1, IGF-2, and the active analogs thereof for the preparation of a medicament for administration to birds in ovo for carrying out the methods described above.

The foregoing and other objects and aspects of the present invention are explained in detail in the specification set forth below.

DETAILED DESCRIPTION OF THE INVENTION

The term "bird" is intended to include males or females of any avian species, but is primarily intended to encompass poultry which are commercially raised for eggs or meat. Accordingly, the term "bird" is particularly intended to encompass hens, cocks and drakes of chickens, turkeys, ducks, geese, quail and pheasant.

As used herein, "IGF-1" and "IGF-2" refer to insulin-like growth factor 1 and 2 from any species, including bovine, ovine, porcine, equine, avian, and preferably human, in native-sequence or in variant form (e.g., analog), and from any source, whether natural, synthetic, or recombinant.

Insulin-like growth factor-1, a somatomedin, is a small protein that has been shown to stimulate growth of a wide range of cells in culture. Human IGF-1 (hIGF-1) has been purified to homogeneity from human serum and its complete amino acid sequence established. The serum mediator of growth hormone action, somatomedin C, has been shown to have an identical sequence to hIGF-1 so that these two are now considered as being synonymous. The amino acid sequence established for hIGF-1 beginning with the N-terminal glycine is:

---

Gly—pro—glu—thr—leu—cys—gly—ala—glu—leu—
val—asp—ala—leu—gin—phe—val—cys—gly—asp—
arg—gly—phe—tyr—phe—asn—lys—pro—thr—gly—
tyr—gly—ser—ser—ser—arg—arg—ala—pro—gin—
thr—gly—ile—val—asp—glu—cys—cys—phe—arg—
ser—cys—asp—leu—arg—arg—leu—glu—met—tyr—
cys—ala—pro—leu—lys—pro—ala—lys—ser—ala—

(SEQ ID NO: 1)

---

Bovine IGF-1 and porcine IGF-1 have identical sequences.

Using the conventional numbering system of the N-terminal glycine being residue #1 and the C-terminal alanine residue #75, ovine and chicken IGF-1 differ from human IGF-1 only as follows:

ovine IGF-1: ala$^{66}$

Chicken IGF-1: ser$^{26}$; lys$^{41}$, gln$^{50}$, ile$^{64}$

Insulin-like growth factor-2 (IGF-2), like IGF-1, is a small protein that has been shown to stimulate growth of cells in culture. In most cases, these biological effects occur following interaction of IGF-2 with the same cellular receptor as that involved in IGF-1 actions. The amino acid sequence established for human IGF-2 (hIGF-2) beginning with the N-terminal alanine is shown below (SEQ ID NO:2). Upper case letters have been used to indicate the amino acids equivalent to the N-terminal 5 amino acids of hIGF-1:

---

Ala—tyr—arg—PRO—SER—GLU—THR—LEU—cys—gly—
gly—glu—leu—val—asp—thr—leu—gln—phe—val—
cys—gly—asp—arg—gly—phe—tyr—phe—ser—arg—
pro—ala—ser—arg—val—ser—arg—arg—ser—arg—
gly—ile—val—glu—glu—cys—cys—phe—arg—ser—
cys—asp—leu—ala—leu—leu—glu—thr—tyr—cys—
ala—thr—pro—ala—lys—ser—glu (SEQ ID NO: 2)

---

Using the conventional numbering system of the N-terminal alanine being residue #1 and the C-terminal glutamic acid being residue #67, bovine, ovine, porcine and chicken IGF-2 differ from human IGF-2 only as follows:

bovine IGF-2: ser$^{32}$; ile$^{35}$; asn$^{36}$ ovine IGF-2: ser$^{32}$; ile$^{35}$; asn$^{36}$; ala$^{62}$ porcine IGF-2: asn$^{36}$ chicken IGF-2: ala$^{1}$ missing; gly$^{3}$; thr$^{4}$; ala$^{5}$; val$^{32}$; gly$^{33}$; asn$^{35}$; asn$^{36}$; ile$^{39}$; asn$^{40}$ Applicants' International Application PCT/AU87/00246 discloses numerous compounds that can be used in practicing this invention, including compounds corresponding to IGF-1 but lacking one to five, preferably three amino acid residues from the N-terminal of the molecule. These can exhibit a substantial increase in biological potency compared with the more complete compounds.

For example, the compound destripeptide bIGF-1 but lacking the amino acid residues gly, pro and glu from the N-terminal, is effective in inhibiting protein breakdown and stimulating both protein synthesis and DNA synthesis in cellular systems at concentrations between 4 and 50 fold lower than required for entire bIGF-1.

For IGF-1 peptides having N-terminal amino acid sequences in common with that of human/bovine/porcine IGF-1, the elimination of between 1 and 5 amino acid residues from the N-terminal also results in enhanced biological potencies. The said N-terminal amino acid sequence is also a feature of the IGF-1 of rat, ovine, and chicken species.

Accordingly in a first aspect of the present invention there is provided a method of enhancing the growth of a bird utilizing an analog of insulin-like growth factor-1 (IGF-1) or factor-2 (IGF-2) wherein at least the glutamic acid residue is absent at position 3 from the N-terminal of IGF-1 or at position 5 or 6 from the N-terminal of IGF-2. It will be understood that in respect of chicken IGF-2 the N-terminal Ala-residue is absent so that the glutamic acid residue is a position 5 from the N-terminal.

Preferably the peptide analog is a human, bovine, ovine, porcine or chicken insulin-like growth factor analog. More preferably the peptide analog is a human insulin-like growth factor-1 analog.

In a another aspect of the present invention, wherein the peptide analog is an insulin-like growth factor-1 analog, in addition at least one of the Gly-, Pro-, or Thr-residues may be absent from the N-terminal in addition to the absence of the glutamic acid residue.

Suitable amino acid residues to replace glutamic acid include glycine, glutamine, leucine, arginine, or lysine.

More preferably the replacement residue for glutamic acid will be a positively charged amino acid residue such as arginine or lysine. Alternatively the glutamic acid residue may be replaced by glycine and the threonine residue normally adjacent to the glutamic acid may be replaced by a different amino acid residue, preferably arginine or glycine, most preferably arginine.

Preferably the N-terminal sequence is selected from

---

| | |
|---|---|
| Val—Leu—Cys— | (SEQ ID NO: 3) |
| Arg—Leu—Cys— | (SEQ ID NO: 4) |
| Gly—Leu—Cys— | (SEQ ID NO: 5) |
| Gly—Thr—Leu—Cys— | (SEQ ID NO: 6) |
| Gly—Pro—Arg—Thr—Leu—Cys— | (SEQ ID NO: 7) |
| Gly—Pro—Gly—Arg—Leu—Cys— | (SEQ ID NO: 8) |
| Gly—Pro—Gly—Gly—Leu—Cys— | (SEQ ID NO: 9) |
| Gly—Pro—Gly—Thr—Leu—Cys— | (SEQ ID NO: 10) |
| Gly—Pro—Gln—Thr—Leu—Cys— | (SEQ ID NO: 11) |
| Gly—Pro—Lys—Thr—Leu—Cys— | (SEQ ID NO: 12) |
| Gly—Pro—Leu—Thr—Leu—Cys— | (SEQ ID NO: 13) |

--- with the Cys residue shown being that normally as position 6 from the N-terminal.

In a another aspect of the present invention the peptide analog is an insulin-like growth factor-2 analog. Preferably in the analog, at least one of the Ala-, Tyr-Arg-, Pro-, Ser- or Thr- residues is absent from the N-terminal in addition to the absence of the glutamic acid residue at position 6.

More preferably the glutamic acid residue is replaced by a different amino acid residue. Suitable amino acid residues to replace glutamic acid include glycine, glutamine, leucine, arginine, or lysine. Suitable amino acid residues to replace the threonine residue include arginine or glycine.

More preferably the replacement residue for glutamic acid will be a positively charged amino acid residue such as arginine or lysine. Alternatively the glutamic acid residue may be replaced by glycine and the threonine residue normally adjacent to the glutamic acid may be replaced by a different amino acid residue, preferably arginine or glycine, most preferably arginine.

Preferably the N-terminal sequence is selected from

---

Ala—Tyr—Arg—Pro—Ser—Lys—Thr—Leu—Cys—
(SEQ ID NO: 14)

Ala—Tyr—Arg—Pro—Ser—Arg—Thr—Leu—Cys—
(SEQ ID NO: 15)

Ala—Tyr—Arg—Pro—Ser—Gly—Arg—Leu—Cys—
(SEQ ID NO: 16)

Ala—Tyr—Arg—Pro—Ser—Gly—Thr—Leu—Cys—
(SEQ ID NO: 17)

--- with the Cys residue shown being that normally at position 9 from the N-terminal.

A specific analog presently preferred is Long R3 IGF-1 (LR$^3$ IGF-1), as disclosed in applicants' International Application PCT/AU90/00210. This analog is an 83 amino acid analog comprising the complete human IGF-1 sequence with the substitution of an Arg for Glu at Position 3 and a 13 amino acid extension peptide at the N-terminus, and has been shown to increase the growth of cultured cells at lower dose rates than required for IGF-1. The sequence of LR$^3$ IGF-1 is:

met—phe—pro—ala—met—pro—leu—ser—ser—leu—phe—
val—asn—gly—pro—arg—thr—leu—cys—gly—ala—glu—
leu—val—asp—ala—leu—gln—phe—val—cys—gly—asp—
arg—gly—phe—tyr—phe—asn—lys—pro—thr—gly—tyr—
gly—ser—ser—ser—arg—arg—ala—pro—gln—thr—gly—
ile—val—asp—glu—cys—cys—phe—arg—ser—cys—asp—
leu—arg—arg—leu—glu—met—tyr—cys—ala—pro—leu—
lys—pro—ala—lys—ser—ala— (SEQ ID NO: 18)

The peptide analogs above may be produced by appropriate modifications to methods existing for the production of the full IGF-1 and IGF-2 peptides. These modifications would be familiar to one skilled in the art. Additional analogs are made by modifying the natural sequence of IGF-1 or IGF-2 of a different species of origin in like manner to those modifications, above, of human IGF-1 and IGF-2.

The active compounds described herein may be administered and prepared as pharmaceutical formulations per se or in the form of pharmaceutically acceptable salts thereof. For example, acid addition salts of acetate, adipate, alginate, aspartate, benzoate, benzenesulfonate, bisulfate, butyrate, citrate, camphorate, camphorsulfonate, cyclopentanepropionate, digluconate, dodecylsulfonate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylproprionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth.

More specifically, the present invention provides a veterinary composition that includes:

(a) an amount of a peptide analog of insulin-like growth factor-1 (IGF-1) or factor-2 (IGF-2) wherein at least the glutamic acid residue is absent at position 3 from the N-terminal of IGF-1 or at position 6 from the N-terminal of IGF-2 respectively, and (b) a pharmaceutically acceptable diluent, carrier or excipient therefor (e.g., sterile pyrogen-free physiological saline solution or sterile pyrogen-free water).

Dosage is not critical and will vary with the species being treated, the time and site of administration, and the desired effect. The upper limit of the dosage can be routinely determined, but may be as much as 250, 1,000, or 2,000 μg or more. The lower limit of the dosage likewise can be routinely determined, but may be as little as 0.5 or 0.1 μg or less.

The term "in ovo," as used herein, refers to birds contained within an egg prior to hatch. Thus, the present invention may be conceived of as both a method of treating eggs and a method of treating birds. The present invention may be practiced with any type of bird egg, including chicken, turkey, duck, goose, quail, and pheasant eggs. Chicken eggs are preferred. Eggs treated by the method of the present invention are treated during the first or last quarter of incubation.

The term "in ovo administration," as used herein, refers to any means which transports the peptide through the shell. The preferred method of administration is, however, by injection. The site of injection can be within the region defined by the amnion, including the amniotic fluid and the embryo itself, in the yolk sac, in the albumen or in the air cell. For practicing the present invention, injection into the aircell or albumen is currently preferred.

The mechanism of injection is not critical, but it is preferred that the method not unduly damage the tissues and organs of the embryo or the extraembryonic membranes surrounding it so that the treatment will not decrease hatch rate. A hypodermic syringe fitted with a needle of about 18–23 gauge is suitable for the purpose. To inject into the air cell, the needle need only be inserted into the egg by about two millimeters. A one inch needle, when fully inserted from the center of the large end of the egg, will penetrate the shell, the outer and inner shell membranes enclosing the air cell, and the amnion. Depending on the precise stage of development and position of the embryo, a needle of this length will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

It is envisioned that a high speed automated injection system for avian embryos will be particularly suitable for practicing the present invention. Numerous such devices are available, exemplary being those disclosed in U.S. Pat. No. 4,681,063 to Hebrank and U.S. Pat. Nos. 4,040,388, 4,469,047, and 4,593,646 to Miller (the disclosures of all U.S. patent references cited herein are to be incorporated herein by reference). All such devices, as adapted for practicing the present invention, comprise an injector containing IGF-1 or its analogs as described herein, with the injector positioned to inject an egg carried by the apparatus with the IGF-1 or its analogs. In addition, if desired, a sealing apparatus operatively associated with the injection apparatus may be provided for sealing the hole in the egg after injection thereof.

Preferred apparatus for practicing the present invention is disclosed in U.S. Pat. No. 4,681,063 to Hebrank and European Patent Application No. 87305746.7 to Embrex, Inc., filed 29 Jun. 1987, the disclosures of which are incorporated herein by reference. This device comprises an injection apparatus for delivering fluid substances into a plurality of eggs and suction apparatus which simultaneously engages and lifts a plurality of individual eggs from their upwardly facing portions and cooperates with the injection means for injecting the eggs while the eggs are engaged by the suction apparatus.

The following examples are provided to more fully illustrate the present invention, and are not to be taken as restrictive thereof.

EXAMPLE 1

In Ovo Administration of IGF-1 Analog on Day 5 of Incubation

This example demonstrates the effect of in ovo administration of an IGF-1 analog, Long R3 IGF-1 (LR$^3$ IGF-1), on day 5 of incubation in chickens.

This experiment consisted of ten treatments, repeated in two trials. Treatments were as follows:

(1) aircell injection, 0.0 μg of LR$^3$ IGF-1;
(2) aircell injection, 0.5 μg of LR$^3$ IGF-1;

(3) aircell injection, 5.0 μg of LR³ IGF-1;
(4) aircell injection, 50 μg of LR³ IGF-1;
(5) aircell injection, 250 μg of LR³ IGF-1;
(6) albumen injection, 0.0 μg of LR³ IGF-1;
(7) albumen injection, 0.5 μg of LR³ IGF-1;
(8) albumen injection, 5.0 μg of LR³ IGF-1;
(9) albumen injection, 50 μg of LR³ IGF-1;
(10) albumen injection, 250 μg of LR³ IGF-1.

The vehicle employed is sterile physiological saline solution. Two trials were conducted investigating the effects of in ovo LR³ IGF-1 administration on Day 5 of incubation. In Trial One, all chicks and unhatched eggs were sacrificed at day 21 of incubation. In Trial Two, posthatch growth data was collected to posthatch day 46.

Trial One:

On Day 0 of incubation, 2197 Peterson X Arbor Acre broiler eggs were set in Jamesway 252 single stage forced draft incubators. Standard temperature and humidity regimes were followed throughout incubation.

On Day 5 of incubation a subset of 600 eggs was removed from the incubator. Sixty eggs were randomly assigned to each of the ten treatment groups. Eggs to be injected included fertile, infertile, and early dead embryonated eggs. LR³ IGF-1 doses tested were either 0, 0.5, 5, 50, or 250 μg. Radioimmunoassay verified the dosages to be 0.494, 5.14, 49.7, and 250.07 μg LR³ IGF-1, respectively. Injection site was either in the aircell or the albumen.

The injection site was first cleaned with a 0.5% chlorine bleach solution. All albumen injections involved turning the eggs upside down, pointed end up, punching a hole in the egg with a 23 gauge needle and then inserting a 23 gauge needle attached to a 1 cc tuberculin syringe at a depth of ¼ inch and delivering 50 μl of test article into the albumen. A new syringe and needle were used for every 20 eggs injected. Needles were not sanitized between injections. All aircell injections utilized an identical technique, except eggs remained right side up and test article was delivered onto the inner shell membrane. Following injection, all injection sites were sealed with Duco cement and returned to the incubator.

On Day 18 of incubation, all eggs were transferred into pedigree hatching baskets, two replicates of 30 eggs per treatment, and placed into Jamesway 252 hatchers. On Day 21 of incubation chicks were removed from the hatcher, counted, weighed and sacrificed. All unhatched eggs were broken open to determine fertility and the stage of embryonic mortality.

Trial Two:

Trial two utilized 1,266 Hubbard X Hubbard broiler eggs. Procedures outlined for trial one were followed during this trial except the number of eggs per treatment group varied from 65 to 178 and chicks were not weighed or sacrificed at hatch. Approximately 50 birds were placed in one pen for each treatment group. Mortality, feed efficiency, and weekly body weight measurements were collected until Day 46 posthatch. The controls for the study were initially a pen of mixed vehicle injected controls (½ aircell, ½ albumen) and a pen of noninjected controls. On Day 25 posthatch, noninjected and vehicle injected controls were mixed. Toxicity following in ovo administration of 250 μg peptide into the albumen of Day 5 embryonated eggs resulted in a poor hatch allowing placement of only nine chicks. Therefore, this data was not included in the final report. A subsample of six males and six females selected for similar body weights were sacrificed. Dead weight, defeathered weight, empty carcass weight, viscera weight, and fat pad weight were determined.

The results of Example 1, trials one and two, as described above are given in Tables 1 to 6, below. Hatchability was not affected following in ovo administration of either 0.5, 5, 50, or 250 μg LR³ IGF-1 into the aircell of five day embryonated broiler eggs in either of the two trials (Table 1). Moreover, vehicle injected controls hatched as well as noninjected controls. In ovo administration of identical concentrations of LR³ IGF-1¼ inch through the bottom of the egg into the albumen decreased hatchability in a dose dependent manner (Table 1). Hatchability was decreased 15% below noninjected controls due to the injection process itself and not LR³IGF-1. Overall hatchability of noninjected control eggs during Trial 1 was 65.3% and 87.5% during Trial 2.

TABLE 1

Hatchability Effects Following LR³ IGF-I Administration In Ovo to Day 5 Embryonated Broiler Eggs

| Site of Injection | In Ovo Treatment LR³ IGF-I (μg) | Hatchability (%) of Noninjected Controls | Eggs Injected |
|---|---|---|---|
| Aircell | Vehicle Controls | 100.5 | 238 |
|  | 0.5 | 109.3 | 158 |
|  | 5.0 | 102.6 | 156 |
|  | 50.0 | 101.4 | 159 |
|  | 250.0 | 102.6 | 159 |
| Albumen | Vehicle Controls | 85.3 | 134 |
|  | 0.5 | 50.6 | 161 |
|  | 5.0 | 68.5 | 134 |
|  | 50.0 | 45.8 | 161 |
|  | 250.0 | 39.7 | 125 |

[1]Means represents one hatchability observation from each of two trials (n = 2).

TABLE 2

Hatch Weight Following In Ovo Administration of LR³ IGF-I to Day 5 Embryonated Broiler Eggs

| Site of Injection | In Ovo Treatment LR³ IGF-I (μg) | Body Weight[1] at Hatch (g) | Chicks Weighed |
|---|---|---|---|
| Aircell | Vehicle Controls | 42$^b$ | (41) |
|  | 0.5 | 44$^a$ | (46) |
|  | 5.0 | 43$^{ab}$ | (41) |
|  | 50.0 | 43$^{ab}$ | (42) |
|  | 250.0 | 43$^{ab}$ | (42) |
| Pooled SEM .2714 |  |  |  |
| Albumen | Vehicle Controls | 42$^{AB}$ | (38) |
|  | 0.5 | 44$^A$ | (18) |
|  | 5.0 | 42$^B$ | (26) |
|  | 50.0 | 44$^{AB}$ | (16) |
|  | 250.0 | 43$^{AB}$ | (25) |
| Pooled SEM .3290 |  |  |  |

[1]Means representative of all chicks which hatched from 60 eggs within one set.
$^{AB}$Means with no common superscripts within a column subset differed significantly according to Duncan's Multiple Range Test (P < .05).
$^{ab}$Means with no common superscripts within a column subset differed significantly according to Duncan's Multiple Range Test (P ≤ .10).

TABLE 3

Body Weights and Feed Efficiency of 46 Day Old Broilers Following In Ovo LR³ IGF-I Administration on Day 5 of Incubation
Body Weight Mean ± SE (n)

| In Ovo Treatment (μg LR³ IGF-I) | Males (g) | Females (g) | Feed Efficiency F/G |
|---|---|---|---|
| Controls | 2320 ± 63 (24) | 1994 ± 28 (25) | 1.76 |
| 0.5 albumen | 2455 ± 53 (19) | 2079 ± 40 (22) | 1.62 |

TABLE 3-continued

Body Weights and Feed Efficiency of 46 Day Old Broilers Following In Ovo LR³ IGF-I Administration on Day 5 of Incubation Body Weight Mean ± SE (n)

| In Ovo Treatment (μg LR³ IGF-I) | Males (g) | Females (g) | Feed Efficiency F/G |
|---|---|---|---|
| 5.0 albumen | 2495 ± 54 (17) | 1984 ± 27 (26) | 1.73 |
| 50.0 albumen | 2388 ± 59 (16) | 1968 ± 27 (26) | 1.77 |
| 0.5 aircell | 2362 ± 36 (17) | 1971 ± 22 (32) | 1.67 |
| 5.0 aircell | 2389 ± 25 (27) | 1959 ± 28 (22) | 1.69 |
| 50.0 aircell | 2316 ± 36 (28) | 1972 ± 29 (22) | 1.69 |
| 250.0 aircell | 2452 ± 43 (25) | 2004 ± 24 (23) | 1.67 |

TABLE 4

Weekly Body Weight Measurement of Broilers Administered LR³ IGF-I on Day 5 of Incubation

| In Ovo Treatment LR³ IGF-I (μg) | \multicolumn{7}{c}{DAY OF AGE} | | | | | | |
|---|---|---|---|---|---|---|---|
| | 4 | 11 | 18 | 25 | 32 | 39 | 46 |
| | \multicolumn{7}{c}{Body Weight[1] (g)} | | | | | | |
| Controls[2] | 69 | 210 | 489 | 808 | 1223 | 1627 | 2080 |
| 0.5 albumen | 69 | 194 | 473 | 817 | 1185 | 1750 | 2253 |
| 5.0 albumen | 69 | 196 | 462 | 818 | 1196 | 1727 | 2103 |
| 50.0 albumen | 69 | 193 | 429 | 754 | 1102 | 1595 | 2044 |
| 0.5 aircell | 71 | 197 | 459 | 746 | 1104 | 1559 | 2033 |
| 5.0 aircell | 70 | 196 | 463 | 800 | 1177 | 1665 | 2118 |
| 50.0 aircell | 68 | 186 | 463 | 806 | 1229 | 1656 | 2165 |
| 250.0 aircell | 68 | 200 | 471 | 784 | 1212 | 1678 | 2159 |

[1]Means represent one pen of approximately 50 birds.
[2]At 32 days posthatch vehicle injected controls (¼ aircell, ¼ albumen) and noninjected controls were mixed.

In ovo administration of 0.5 μg LR³ IGF into the aircell of five day embryonated broiler eggs significantly increased hatch weight ($P \leq 0.10$) over vehicle injected controls (Table 2). Injection of either 5, 50, or 250 μg LR³ IGF-1 also resulted in slight numerically increased hatch weights (Table 2). There was no significant effect on hatch weight following in ovo injection of either 0.5, 5, 50, or 250 μg LR³ IGF-1 into the albumen of Day 5 embryonated eggs, however there was a trend for all treated chicks to weigh more (Table 2).

Male broilers 46 days of age which had been injected with either 0.5, 5, or 50 μg LR³ IGF-1 into the albumen on Day 5 of incubation exhibited a dose related body weight increase (Table 3). Increased body weight was not demonstrated in females except at the lowest dose, 0.5 μg LR³ IGF-1. LR³ IGF-1 administration into the aircell of Day 5 embryonated broilers only increased Day 46 body weights at the highest dose, 250 μg. Once again, the effect was only demonstrated in males, not females (Table 3).

Feed efficiency was variable due to small n numbers and unevenly distributed sex ratios. However, the feed-to-gain ratio of broilers administered 0.5 μg LR³ IGF-1 into the albumen was low compared to controls as well as all other treatment groups (Table 3). Expected six week feed conversion values for Peterson X Arbor Acre broilers are 1.72 and 1.77 for males and females respectively.

Body weights were extremely tight across all treatment groups considering the small number of birds examined. Treatment related differences in body weights did not appear until late in the growout period, Day 39 posthatch (Table 4).

Positive growth effects due to peptide treatment could not be attributed to increased visceral weight as often evidenced in growth hormone treated animals

TABLE 5

Effect of LR³ IGF-I Administered In Ovo on Day 5 of Incubation on Selected Carcass Parameters of Male Broilers[1]

| In Ovo Treatment LR³ IGF-I (μg) | Dead Weight | Defeathered Weight | Empty Carcass Weight (g) | Viscera Weight | Fat Pad Weight | Relative Fat Pad Weight (%) |
|---|---|---|---|---|---|---|
| Controls | 2361 | 2143 (91%) | 1844 (78%) | 250.8 (10.6%) | 62.2 | 2.64 |
| 0.5 albumen | 2330 | 2092 (90%) | 1793 (77%) | 231.8 (9.9%) | 47.9 | 2.04 |
| 5.0 albumen | 2404 | 2142 (89%) | 1828 (76%) | 263.2 (10.9%) | 55.5 | 2.30 |
| 50 albumen | 2399 | 2181 (91%) | 1854 (77%) | 270.8 (11.3%) | 58.1 | 2.39 |
| 0.5 aircell | 2429 | 2210 (91%) | 1834 (76%) | 282.2 (11.6%) | 57.7 | 2.37 |
| 5.0 aircell | 2451 | 2199 (90%) | 1926 (79%) | 266.0 (10.9%) | 50.0 | 2.04 |
| 50 aircell | 2429 | 2189 (90%) | 1878 (77%) | 273.8 (11.3%) | 61.6 | 2.54 |
| 250 aircell | 2368 | 2137 (90.2%) | 1859 (79%) | 250.5 (10.6%) | 61.6 | 2.60 |

[1]Means represent 6 birds selected from each treatment group by sex and comparable body weights.

TABLE 6

Effect of LR³ IGF-I Administered In Ovo on Day 5 of Incubation on Selected Carcass Parameters of Female Broilers[1]

| In Ovo Treatment LR³ IGF-I (μg) | Dead Weight | Defeathered Weight | Empty Carcass Weight | Viscera Weight | Fat Pad Weight | Relative Fat Pad Weight |
|---|---|---|---|---|---|---|
| Controls | 2040 | 1864 (91%) | 1611 (79%) | 224.2 (11.0%) | 66.6 | 3.27 |
| 0.5 albumen | 1948 | 1748 (90%) | 1487 (76%) | 218.3 (11.2%) | 55.7 | 2.86 |
| 5.0 albumen | 1943 | 1765 (91%) | 1523 (78%) | 205.7 (10.6%) | 61.2 | 3.14 |
| 50 albumen | 1997 | 1815 (91%) | 1544 (77%) | 231.8 (11.6%) | 58.4 | 2.91 |
| 0.5 aircell | 2055 | 1872 (91%) | 1590 (77%) | 237.0 (11.5%) | 54.2 | 2.64 |
| 5.0 aircell | 2056 | 1864 (91%) | 1593 (77%) | 236.2 (11.5%) | 61.7 | 3.01 |
| 50 aircell | 2044 | 1836 (90%) | 1555 (76%) | 236.7 (11.6%) | 53.5 | 2.61 |
| 250 aircell | 1956 | 1776 (91%) | 1509 (77%) | 225.8 (11.5%) | 64.3 | 3.28 |

[1]Means represent 6 birds selected from each treatment group by sex and comparable body weights.

(Tables 5 and 6). An injection of 0.5 μg LR³IGF-1 into the albumen on Day 5 of incubation numerically decreased relative fat pad weights in both male and female broilers (Tables 5 and 6).

These results indicate that in ovo administration of LR³ IGF-1 on day 5 of incubation dramatically increased posthatch growth of male broilers (Table 3). The enhanced growth occurred during the last phase of grow-out, weeks 5-7 (Table 4). The effective doses were either 0.5 or 5.0 μg of peptide injected into the albumen, or 250 μg LR³ IGF-1 injected into the aircell.

Additionally, feed efficiency and fat pad percentage were both reduced following injection of 0.5 μg of LR³ IGF-1 into the albumen, but these parameters were not as clearly affected by the other treatments that positively affected growth (e.g., 5.0 μg into the albumen or 250 μg into the aircell). It appears that increased growth responses are not due to increased visceral weight or increased abdominal fat deposition.

EXAMPLE 2

In Ovo Administration of IGF-1 Analog on Day 13 of Incubation

This example demonstrates the effect of in ovo administration of an IGF-1 analog on day 13 of incubation in chickens. The specific analog chosen for this study was Long R3 IGF-1 (LR³ IGF-1).

This experiment consisted of fourteen treatments, as follows:

(1) aircell injection, 0.0 μg of LR³ IGF-1;
(2) aircell injection, 0.5 μg of LR³ IGF-1;
(3) aircell injection, 5.0 μg of LR³ IGF-1;
(4) aircell injection, 50 μg of LR³ IGF-1;
(5) aircell injection, 250 μg of LR³ IGF-1;
(6) albumen injection, 0.0 μg of LR³ IGF-1;
(7) albumen injection, 0.5 μg of LR³ IGF-1;
(8) albumen injection, 5.0 μg of LR³ IGF-1;
(9) albumen injection, 50 μg of LR³ IGF-1;
(10) amniotic cavity injection, 0.0 μg of LR³IGF-1.
(11) amniotic cavity injection, 0.5 μg of LR³IGF-1.
(12) amniotic cavity injection, 5.0 μg of LR³IGF-1.
(13) amniotic cavity injection, 50 μg of LR³IGF-1.
(14) amniotic cavity injection, 250 μg of LR³ IGF-1.

This experiment utilized Peterson X Arbor Acre broiler eggs. Infertile, early, and middle dead embryonated eggs were not separated out. Sixty eggs per treatment group were injected according to the treatments, above. Aircell and albumen injections were performed as indicated in Example 1, above; amniotic cavity injections were made one inch through the large end of the egg into the amniotic cavity. Chicks were weighed at hatching and then sacrificed.

The results are given in Tables 7-8. Hatchability effects following in ovo administration of LR³ IGF-1 on Day 13 of incubation was site and dose specific. No effect on hatchability was observed for aircell or albumen injections (Table 7). Similarly, egg injection itself into either the aircell or albumen did not adversely effect hatchability. However, hatchability was depressed following injection into the amnion.

TABLE 7

Hatchability Effects Following LR³ IGF-I Administration In Ovo to 13 Day Embryonated Broiler Eggs

| Site of Injection | In Ovo Treatment LR³ IGF-I (μg) | Hatchability % of Noninjected Controls | Eggs Injected |
|---|---|---|---|
| Aircell | Vehicle Controls | 101.6 | 60 |
| | 0.5 | 99.0 | 60 |
| | 5.0 | 106.7 | 60 |
| | 50.0 | 101.6 | 60 |
| | 250.0 | 111.7 | 60 |
| Albumen | Vehicle Controls | 121.9 | 60 |
| | 0.5 | 73.1 | 60 |
| | 5.0 | 94.0 | 60 |
| | 50.0 | 106.7 | 60 |
| Amnion | Vehicle Controls | 91.4 | 60 |
| | 0.5 | 71.1 | 60 |
| | 5.0 | 66.0 | 60 |
| | 50.0 | 88.9 | 60 |
| | 250.0 | 40.6 | 60 |

TABLE 8

Hatch Weight Following In Ovo Administration of LR³ IGF-I to Day 13 Embryonated Broiler Eggs

| Site of Injection | In Ovo Treatment LR³ IGF-I (μg) | Body Weight at Hatch (g) | Chicks[1] Weighed |
|---|---|---|---|
| Aircell | Vehicle Controls | 43$^{AB}$ | (40) |
| | 0.5 | 43$^{B}$ | (39) |
| | 5.0 | 45$^{A}$ | (42) |
| | 50.0 | 44$^{AB}$ | (40) |
| | 250.0 | 43$^{AB}$ | (44) |
| Pooled SEM .2736 | | | |
| Albumen | Vehicle Controls | 42$^{AB}$ | (48) |
| | 0.5 | 44$^{A}$ | (29) |
| | 5.0 | 42$^{A}$ | (37) |
| | 50.0 | 44$^{AB}$ | (42) |
| Pooled SEM .2954 | | | |
| Amnion | Vehicle Controls | 43$^{B}$ | (36) |
| | 0.5 | 44$^{AB}$ | (28) |
| | 5.0 | 43$^{B}$ | (26) |
| | 50.0 | 43$^{B}$ | (35) |
| | 250.0 | 46$^{A}$ | (16) |
| Pooled SEM .3126 | | | |

[1]Means representative of all chicks which hatched from 60 eggs within one set.
$^{AB}$Means with no common superscripts within a column subset differed significantly according to Duncan's Multiple Range Test (P ≤ .05).
$^{ab}$Means with no common superscripts within a column subset differed significantly according to Duncan's Multiple Range Test (P ≤ .10).

TABLE 9

Hatchability Effects Following LR³ IGF-I Administration In Ovo to Day 17 Embryonated Broiler Eggs

| Site of Injection | In Ovo Treatment LR³ IGF-I (μg) | Hatchability[1] % of Noninjected Controls | Eggs Injected |
|---|---|---|---|
| Aircell | Vehicle Controls | 94.2 | 186 |
| | 0.5 | 91.2 | 172 |
| | 5.0 | 99.9 | 172 |
| | 50.0 | 95.2 | 194 |
| | 250.0 | 94.4 | 192 |
| Albumen | Vehicle Controls | 88.5 | 160 |
| | 0.5 | 88.4 | 148 |
| | 5.0 | 80.9 | 149 |
| | 50.0 | 90.4 | 148 |
| | 250.0 | 76.9 | 147 |

[1]Means represent one hatchability observation from each of two trials (n = 2).

TABLE 10

Hatch Weight Following In Ovo Administration of LR³ IGF-I to Day 17 Embryonated Broiler Eggs

| Site of Injection | In Ovo Treatment LR³ IGF-I (μg) | Body Weight at Hatch (g) | Chicks[1] Weighed |
|---|---|---|---|
| Aircell | Vehicle Controls | 43[a] | (46) |
| | 0.5 | 42[b] | (42) |
| | 5.0 | 43[ab] | (51) |
| | 50.0 | 42[ab] | (45) |
| | 250.0 | 43[a] | (46) |
| Pooled SEM .2298 | | | |
| Amnion | Vehicle Controls | 44[a] | (48) |
| | 0.5 | 44[b] | (29) |
| | 5.0 | 44[ab] | (37) |
| | 50.0 | 44[ab] | (42) |
| | 250.0 | 42[b] | (36) |
| Pooled SEM .2629 | | | |

[1]Means represent weight of all chicks hatched from 60 eggs within one set.
[ab]Means with no common superscripts within a column subset differed significantly according to Duncan's Multiple Range Test (P ≦ .10).

TABLE 11

Two Week Body Weights[1] and Mortality[1] Following In Ovo Administration of LR³ IGF-I to Day 17 Embryonated Broiler Eggs

| Site of Injection | In Ovo Treatment LR³ IGF-I μg | Two Week Body Weight (g) | Mortality (%) | Chicks Weighed |
|---|---|---|---|---|
| Aircell | Vehicle Controls | 358 | 0.8 | 130 |
| | 0.5 | 361 | 0 | 128 |
| | 5.0 | 356 | 3.0 | 133 |
| | 250.0 | 365 | 1.5 | 130 |
| Pooled SEM 3.413 | | | | |
| Amnion | Vehicle Controls | 369[A] | 1.6 | 123 |
| | 0.5 | 366[A] | 1.6 | 125 |
| | 5.0 | 361[AB] | 4.1 | 112 |
| | 250.0 | 352[B] | 6.5 | 98 |
| Pooled SEM 3.407 | | | | |

[1]Means represent pooled results of one growout study of approximately 30 commingled chicks and one of approximately 100 commingled chicks.
[AB]Means with no common superscripts within a column subset differed significantly according to Duncan's Multiple Range Test (P ≦ .05).

TABLE 12

Two Week Body Weights and Mortality Following In Ovo Administration of 50 μg LR³ IGF-I into the Aircell of Day 17 Broiler Eggs

| In Ovo Treatment LR³ IGF-I (μg) | Two Week Body Weight (g) | Chicks Weighed[1] |
|---|---|---|
| Noninjected Controls | 369 | 97 |
| Vehicle Controls | 369 | 100 |
| 50 μg IGF | 382 | 98 |

[1]Means representative of one individual growout study of commingled birds.

TABLE 13

Six Week Body Weights and Mortality of Broilers Following In Ovo Administration of LR³ IGF-I into the Aircell on Day 17 of Incubation

| In Ovo Treatment LR³ IGF-I (μg) | Six Week Body Weight (g) | Mortality (%) | Chicks Weighed |
|---|---|---|---|
| Noninjected Controls | 2010[b] | 2.0 | 95 |
| Vehicle Controls | 2049[ab] | 1.0 | 97 |
| 0.5 | 2044[ab] | 1.0 | 93 |
| 5.0 | 2044[ab] | 4.0 | 93 |
| 50.0 | 2079[a] | 1.0 | 97 |
| 250.0 | 2073[ab] | 2.0 | 95 |
| Pooled SEM = 10.1631 | | | |

[1]Means representative of one growout trial of commingled chicks.
[ab]Means with different superscripts differ significantly according to Duncan's Multiple Range Test (P ≦ .10).

Hatch weights, indicative of embryonic growth, were not significantly affected by in ovo administration of either 0.5, 5, 50, or 250 μg LR³ IGF-1 into the aircell, 0.5, 5, or 50 μg LR³ IGF-1 into the albumen or 0.5, 5, or 50 μg LR³ IGF-1 into the amnion. Injection of 250 μg LR³ IGF-1 into the amnion resulted in significantly (P≦0.05) increased hatch weights, however, this same treatment deleteriously affected hatchability.

Note that hatchability and hatch weight results (Tables 7 and 8) indicate LR³ IGF-1 can be administered into the aircell without negatively affecting hatchability.

EXAMPLE 3

In Ovo Administration of IGF-1 Analog on Day 17 of Incubation

Example Three demonstrates the effect on hatchability and hatch weight of in ovo administration of an IGF-1 analog on day 17 of incubation in chickens. The specific analog chosen for this study was Long R3 IGF-1 (LR3 IGF-1).

Example Three consisted of two trials, each trial consisting of ten treatments conducted in Day 17 embryonated broiler eggs, as follows:

(1) aircell injection, 0.0 μg LR³ IGF-1
(2) aircell injection, 0.5 μg LR³ IGF-1
(3) aircell injection, 5.0 μg LR³ IGF-1
(4) aircell injection, 50 μg LR³ IGF-1
(5) aircell injection, 250 μg LR³ IGF-1
(6) amnion injection, 0.0 μg LR³ IGF-1
(7) amnion injection, 0.5 μg LR³ IGF-1
(8) amnion injection, 5.0 μg LR³ IGF-1
(9) amnion injection, 50 μg LR³ IGF-1
(10) amnion injection, 250 μg LR³ IGF-1

Example three used only live embryonated Peterson X Arbor Acre eggs; all infertiles, early, and middle dead embryonated eggs were withdrawn from the study. Eggs were injected according to the method described in Examples 1 and 2, except the injection site was not sealed and an 18 gauge punch and 22 gauge needle were utilized. Two trials were conducted. Fifty-two eggs per treatment group were observed during Trial 1 and 95–142 eggs per treatment group were observed during Trial 2.

Hatchability effects were assessed during both trials of Example Three; hatch weights were collected only during Trial 1. Two week growth and mortality was assessed for each trial. There was confusion concerning birds injected with 50 μg LR³ IGF-1 during Trial 1, therefore, these treatments were deleted from the two week body weight results. In Trial 1, approximately 30 chicks per treatment group were reared in a Petersime battery. All treatment groups were commingled. During Trial 2 approximately 100 chicks per treatment group were reared in floor pens. All treatment groups were commingled. Additionally, broilers which had been injected into the aircell with LR³ IGF-1 were grown to six weeks of age. All birds were fed a high protein ration (30%) during the entire growout. Feed was nonmedicated and birds were not vaccinated.

The results of an experiment as described in Example 3, above, are given in Tables 9 to 13, below. Hatchability following in ovo administration of either 0.5, 5, 50 or 250 μg LR³ IGF-1 into the aircell of 17 day embryonated broiler eggs was not significantly affected. Hatchability of amnion-injected day 17 eggs was slightly depressed. Amnion injection of the highest dose of LR³ IGF-1, 250 μg, depressed hatchability 11.6% below vehicle injected controls (Table 9).

In each of two trials conducted, two week body weights were increased following injection of 250 μg LR³ IGF-1 into the aircell of 17 day embryonated broiler eggs, yet decreased in a dose dependent manner following injection into the amnion (Table 11). Two week mortality also increased following administration of peptide into the amnion on day 17 of incubation (Table 11). Two week weights of broilers injected with 50 μg of LR³ IGF-1 into the aircell were not measured during Trial one because of a possible mix-up between treatment groups. However, results from the second trial indicated a positive growth response at two weeks (Table 12).

Six week weight data indicated positive growth effects continued to six weeks of age following injection of either 50 or 250 μg LR³ IGF-1 into the aircell of day 17 embryonated broiler eggs (Table 13). No effects on six week mortality were evident (Table 13).

Note that posthatch growth was enhanced following in ovo administration of either 50 or 250 μg LR³ IGF-1 into the aircell of 17 day embryonated broiler eggs. Lower doses, 5.0 or 0.5 μg, had no effect on posthatch growth.

EXAMPLE 4

In Ovo Administration of IGF-1 Analog on Day 18 of Incubation

Example Four demonstrates the effects of IGF-1 injection in day 18 embryonated chicken broiler eggs on plasma glucose levels, plasma IGF-1 levels, and liver weight. The specific analog chosen for this study was Long R3 IGF-1 (LR³ IGF-1). Two treatments were used, as follows:

(1) aircell injection, 250 μg LR³ IGF-1
(2) amnion injection, 250 μg LR³ IGF-1

This experiment used Peterson X Arbor Acre broiler eggs, with 240 eggs in each of the two treatment groups.

Vehicle injected controls for each site of injection were included in the study. Plasma samples were collected from ten embryos per treatment group via the chorioallantoic veins at 0.25, 1, 8, 24, 48, and 72 hours following LR³ IGF-1 administration. EDTA was the anticoagulant. Blood samples remained on ice until centrifugation to separate cells from plasma. Plasma was collected and stored at −70° C. until analysis for IGF-1 and glucose levels. Plasma IGF-1 levels were determined by radioimmunoassay. Embryos were removed from the shell, weighed, and sacrificed. Livers were dissected out, weighed and immediately frozen on dry ice.

Liver and body weights collected from embryos 15 minutes, 1, 8, 24, 48 and 72 hours following in ovo administration of 250 μg LR³ IGF-1 into either the aircell or amnion were not different from vehicle injected controls (data not shown).

Both the time and level of absorption of IGF-1 by the embryo differed with site of injection (data not shown). Plasma IGF-1 levels following in ovo administration of 250 μg into the aircell were highest immediately following injection, 15 minutes to one hour, and dissipated slowly thereafter. Plasma IGF-1 levels were still elevated above natural levels at hatch, 72 hours after injection. Plasma IGF-1 levels following administration of 250 μg peptide into the amnion peaked at 48 hours following injection on day 18 of incubation and then dropped off precipitously by hatching. However, as seen following aircell injections, plasma IGF-1 levels of treated embryos were still elevated above vehicle injected controls. The peak mean plasma IGF-1 levels following amnion and aircell administration of 250 μg of LR3 IGF-1 were 533 and 77 respectively, indicating a seven fold increase in LR³ IGF-1 absorbed following injection into the amnion.

Vehicle injected embryos exhibited a slight decline in plasma glucose levels during hatching, 24 to 72 hours postinjection (data not shown). Exogenous LR³IGF-1 had no effect on plasma glucose levels following injection of 250 μg into the aircell on day 18 of incubation. However injection of 250 μg of peptide into the amnion resulted in a precipitous drop in plasma glucose levels, falling from 267 to 206 to 169 to 135 μg % at 8, 24, 48 and 72 hours.

The foregoing examples are illustrative of the present invention, and are not to be construed as limiting thereof. The invention is defined by the following claims, with equivalents of the claims to be included therein.

---

That which is claimed is:

1. A method of enhancing the growth of a bird comprising:
   (a) administering a compound selected from the group consisting of IGF-1, IGF-2 and active analogs thereof to a bird in ovo; then
   (b) incubating said bird to hatch; and then
   (c) growing said bird for at least three weeks after hatch,
   wherein said compound is administered in ovo in an amount sufficient to enhance the growth of said bird at least three weeks after hatch.

2. A method according to claim 1 wherein said compound is an analog of IGF-1 lacking one to five amino acid residues from the N-terminal of the molecule.

3. A method according to claim 1 wherein said compound is an analog of IGF-1 wherein the glutamic acid residue at position 3 from the N-terminal of the molecule is either absent or replaced by an amino acid selected from the group consisting of glycine, glutamine, leucine, arginine, and lysine.

4. A method according to claim 3 wherein at least one Gly-, Pro-, or Thr- residue is absent from the N-terminal of the molecule.

5. A method according to claim 4 wherein said glutamic acid residue is replaced by glycine, and the threonine residue normally adjacent to the glutamic acid is optionally replaced by arginine or glycine.

6. A method according to claim 1 wherein said compound is an IGF-1 analog and the N-terminal sequence of said compound is selected from the group consisting of:
   Val-Leu-Cys- (SEQ ID NO:3),
   Arg-Leu-Cys- (SEQ ID NO:4),
   Gly-Leu-Cys- (SEQ ID NO:5),
   Gly-Thr-Leu-Cys-(SEQ ID NO:6),
   Gly-Pro-Arg-Thr-Leu-Cys- (SEQ ID NO:7),
   Gly-Pro-Gly-Arg-Leu-Cys- (SEQ ID NO:8),
   Gly-Pro-Gly-Gly-Leu-Cys- (SEQ ID NO:9),
   Gly-Pro-Gly-Thr-Leu-Cys- (SEQ ID NO:10),
   Gly-Pro-Gln-Thr-Leu-Cys- (SEQ ID NO:11),
   Gly-Pro-Lys-Thr-Leu-Cys- (SEQ ID NO:12), and
   Gly-Pro-Leu-Thr-Leu-Cys- (SEQ ID NO:13),
   wherein the Cys residue shown is that normally in position 6 from the N-terminal.

7. A method according to claim 1 wherein said compound is an analog of IGF-2 wherein the glutamic acid residue is at position 5 or 6 from the N-terminal of the molecule is either absent or is replaced by an amino acid selected from the group glycine, glutamine, leucine, arginine, or lysine.

8. A method according to claim 7 wherein at least one Ala-, Tyr-, Arg-, Pro-, Ser- or Thr- Residues is absent from the N-terminal of the molecule.

9. A method according to claim 8 wherein said glutamic acid residue is replaced by glycine and the threonine residue normally adjacent to the glutamic acid is optionally replaced by arginine or glycine.

10. A method according to claim 1 wherein said compound is an IGF-2 analog and the N-terminal sequence of said compound is selected from the group consisting of:
    Ala-Tyr-Arg-Pro-Ser-Lys-Thr-Leu-Cys- (SEQ ID NO:14),
    Ala-Tyr-Arg-Pro-Ser-Arg-Thr-Leu-Cys- (SEQ ID NO:15),
    Ala-Tyr-Arg-Pro-Ser-Gly-Arg-Leu-Cys- (SEQ ID NO:16), and
    Ala-Tyr-Arg-Pro-Ser-Gly-Thr-Leu-Cys- (SEQ ID NO:17).

11. A method according to claim 1 wherein said compound has the sequence:

met—phe—pro—ala—met—pro—leu—ser—ser—leu—phe—
val—asn—gly—pro—arg—thr—leu—cys—gly—ala—glu—
leu—val—asp—ala—leu—gln—phe—val—cys—gly—asp—
arg—gly—phe—tyr—phe—asn—lys—pro—thr—gly—tyr—
gly—ser—ser—ser—arg—arg—ala—pro—gln—thr—gly—
ile—val—asp—glu—cys—cys—phe—arg—ser—cys—asp—
leu—arg—arg—leu—glu—met—tyr—cys—ala—pro—leu—
lys—pro—ala—lys—ser—ala          (SEQ ID NO: 18).

12. A method according to claim 1, wherein said bird is selected from the group consisting of chickens, turkeys, ducks, geese, quail, and pheasant.

13. A method according to claim 1, wherein said bird is a chicken.

14. A method according to claim 1 wherein said growth is an increase in weight.

15. A method according to claim 1, wherein administration step is carried out by injecting said compound into the amnion, the aircell, or the albumen of the egg.

16. A method according to claim 1 wherein said compound is administered to said egg during the first quarter of incubation.

17. A method according to claim 1 wherein said compound is administered to said egg during the last quarter of incubation.

18. A method according to claim 1 wherein said compound is administered in an amount of from 0.1 μg to 1,000 μg.

19. A method according to claim 1 wherein said compound is administered in an amount of from 0.5 μg to 250 μg.

20. A method of enhancing the growth of a chicken comprising:
(a) administering a compound selected from the group consisting of IGF-1, IGF-2 and active analogs thereof to said chicken in ovo by injection into the egg albumen or aircell; then
(b) incubating said chicken to hatch; then
(c) growing said chicken for at least three weeks after hatch, wherein said compound is administered in ovo in an amount sufficient to enhance the growth of said chicken at least three weeks after hatch.

21. A method according to claim 20 wherein said growth is an increase in weight.

22. A method according to claim 20 wherein said compound is administered to said egg during the first quarter of incubation.

23. A method according to claim 20 wherein said compound is administered to said egg during the last quarter of incubation.

24. A method according to claim 20 wherein said compound is administered in an amount of from 0.1 μg to 1,000 μg.

25. A method according to claim 20 wherein said compound is administered in an amount of from 0.5 μg to 250 μg.

26. A method according to claim 20 wherein said compound is an analog of IGF-1 lacking one to five amino acid residues from the N-terminal of the molecule.

27. A method according to claim 20 wherein said compound is an analog of IGF-1 wherein the glutamic acid residue at position 3 from the N-terminal of the molecule is either absent or replaced by an amino acid selected from the group consisting of glycine, glutamine, leucine, arginine, and lysine.

28. A method according to claim 27 wherein at least one of the Gly-, Pro-, or Thr- residues is absent from the N-terminal of the molecule.

29. A method according to claim 27 wherein the glutamic acid residue is replaced by glycine and the threonine residue normally adjacent to the glutamic acid may be replaced by arginine or glycine.

30. A method according to claim 20 wherein said compound is an IGF-1 analog and the N-terminal sequence of said compound is selected from the group consisting of:
Val-Leu-Cys- (SEQ ID NO:3),
Arg-Leu-Cys- (SEQ ID NO:4),
Gly-Leu-Cys- (SEQ ID NO:5),
Gly-Thr-Leu-Cys- (SEQ ID NO:6),
Gly-Pro-Arg-Thr-Leu-Cys- (SEQ ID NO:7),
Gly-Pro-Gly-Arg-Leu-Cys- (SEQ ID NO:8),
Gly-Pro-Gly-Gly-Leu-Cys- (SEQ ID NO:9),
Gly-Pro-Gly-Thr-Leu-Cys- (SEQ ID NO:10),
Gly-Pro-Gln-Thr-Leu-Cys- (SEQ ID NO:11),
Gly-Pro-Lys-Thr-Leu-Cys- (SEQ ID NO:12), and
Gly-Pro-Leu-Thr-Leu-Cys- (SEQ ID NO:13),
wherein the Cys residue shown is that normally in position 6 from the N-terminal.

31. A method according to claim 20 wherein said compound is an analog of IGF-2 wherein the glutamic acid residue at position 5 or 6 from the N-terminal of the molecule is either absent-or replaced by an amino acid selected from the group glycine, glutamine, leucine, arginine, or lysine.

32. A method according to claim 31 wherein at least one of the Ala-, Tyr-, Arg-, Pro-, Ser- or Thr- Residues is absent from the N-terminal of the molecule.

33. A method according to claim 32 wherein said glutamic acid residue is replaced by glycine and the threonine residue normally adjacent to the glutamic acid is optionally replaced by arginine or glycine.

34. A method according to claim 20 wherein said compound is an IGF-2 analog and the N-terminal sequence of said compound is selected from the group consisting of:
Ala-Tyr-Arg-Pro-Ser-Lys-Thr-Leu-Cys- (SEQ ID NO:14),
Ala-Tyr-Arg-Pro-Ser-Arg-Thr-Leu-Cys- (SEQ ID NO:15),
Ala-Tyr-Arg-Pro-Ser-Gly-Arg-Leu-Cys- (SEQ ID NO:16), and
Ala-Tyr-Arg-Pro-Ser-Gly-Thr-Leu-Cys- (SEQ ID NO:17).

35. A method according to claim 20 wherein said compound has the sequence:

met—phe—pro—ala—met—pro—leu—ser—ser—leu—phe—
val—asn—gly—pro—arg—thr—leu—cys—gly—ala—glu—
leu—val—asp—ala—leu—gln—phe—val—cys—gly—asp—
arg—gly—phe—tyr—phe—asn—lys—pro—thr—gly—tyr—
gly—ser—ser—ser—arg—arg—ala—pro—gln—thr—gly—
ile—val—asp—glu—cys—cys—phe—arg—ser—cys—asp—
leu—arg—arg—leu—glu—met—tyr—cys—ala—pro—leu—
lys—pro—ala—lys—ser—ala        (SEQ ID NO: 18).

* * * * *